(12) United States Patent
Egeler et al.

(10) Patent No.: US 9,260,684 B1
(45) Date of Patent: Feb. 16, 2016

(54) CELL CULTURE DEVICE

(75) Inventors: Oliver Egeler, North Vancouver (CA); Steven Woodside, Calgary (CA)

(73) Assignee: Stemcell Technologies Inc., Vancouver, BC (CA)

( * ) Notice: Subject to any disclaimer, the term of this patent is extended or adjusted under 35 U.S.C. 154(b) by 422 days.

(21) Appl. No.: 13/293,714

(22) Filed: Nov. 10, 2011

Related U.S. Application Data

(60) Provisional application No. 61/412,622, filed on Nov. 11, 2010.

(51) Int. Cl.
*C12M 1/32* (2006.01)
*C12M 1/00* (2006.01)
*B01L 3/00* (2006.01)

(52) U.S. Cl.
CPC ............... *C12M 23/12* (2013.01); *C12M 23/34* (2013.01); *B01L 3/5085* (2013.01); *B01L 2300/08* (2013.01); *B01L 2300/0851* (2013.01); *B01L 2300/0858* (2013.01); *B01L 2300/0893* (2013.01)

(58) Field of Classification Search
CPC .............. B01L 3/5085; B01L 2300/08; B01L 2300/0851; B01L 2300/0858; B01L 2300/0893; C12M 23/12; C12M 23/16; C12M 23/34
USPC ........................................................ 435/305.2
See application file for complete search history.

(56) References Cited

U.S. PATENT DOCUMENTS

| | | | |
|---|---|---|---|
| 2002/0001855 A1* | 1/2002 | Prentiss et al. | 436/526 |
| 2003/0104494 A1* | 6/2003 | Ravkin et al. | 435/7.9 |
| 2007/0292312 A1* | 12/2007 | Bachman et al. | 422/82 |
| 2009/0170190 A1* | 7/2009 | Nishi et al. | 435/299.1 |
| 2009/0298166 A1* | 12/2009 | Fang et al. | 435/305.2 |

FOREIGN PATENT DOCUMENTS

WO 2008106771 9/2008

* cited by examiner

*Primary Examiner* — Michael Marcheschi
*Assistant Examiner* — Gautam Prakash
(74) *Attorney, Agent, or Firm* — Bereskin & Parr LLP/S.E.N.C.R.L., s.r.l.; I. Laurence MacPhie

(57) ABSTRACT

A cell culture device comprises a well. A plurality of microwells are within the well, and a first common fluid volume is within the well above the microwells. A set of sub-microwells are within each microwell, and a second common fluid volume is within each microwell above the set of sub-microwells.

30 Claims, 17 Drawing Sheets

A

B

CELL CULTURE DEVICE

This application claims the benefit of U.S. Provisional Application No. 61/412,622, filed Nov. 11, 2010, the entire contents of which are incorporated herein by this reference to it.

FIELD

The disclosure relates to cell culture devices. Specifically, the disclosure relates to cell culture devices, such as multi-well plates, usable for colony forming assays.

INTRODUCTION

The following is not an admission that anything discussed below is prior art or part of the common general knowledge of persons skilled in the art.

Colony forming cell (CFC) assays of non-adherent cells are typically performed in a semisolid or gelatinous medium that prevents the movement of cells by convective fluid flow, and thus limits the distance that daughter cells move from the location of the parent cell. This results in the formation of a multi-cell colony derived from a single cell as the daughter cells continue to divide. Colony forming assays may provide quantitative information on the number of individual viable progenitor cells in a sample, and allow the isolation and sampling of individual colonies for sub-cloning or further analysis. In the case of stem cells or progenitor cells, CFC assays may also allow classification of colonies into different lineages based on morphology. Thus, CFC assays may allow for both quantification and lineage identification of progenitor cells in a sample.

Microwell devices have also been used for CFC assays. Such devices are intended to entrap individual cells at a defined location to allow for their manipulation and study.

SUMMARY

The following summary is provided to introduce the reader to the more detailed discussion to follow. The summary is not intended to limit or define the claims.

According to one aspect, a cell culture device comprises a well. A plurality of microwells are within the well, and a first common fluid volume is within the well above the microwells. A set of sub-microwells may be within each microwell, where a second common fluid volume is within each microwell above the set of sub-microwells.

The well may be defined at least in part by at least one well sidewall, and a well bottom wall. Each microwell may be defined at least in part by at least one microwell sidewall extending upwardly from the well bottom wall. Each sub-microwell may be defined at least in part by at least one sub-microwell sidewall extending upwardly from the well bottom wall. Each sub-microwell may be further defined by a portion of one of the microwell sidewalls.

The well bottom wall may be transparent or translucent.

Each set of sub-microwells may comprise four sub-microwells arranged in a 2×2 array. In alternate examples, the sub-microwells are arranged in another configuration, such as a 2×1, 3×1, 3×2, 3×3 or larger array.

Each sub-microwell may comprise a sub-microwell top portion and a sub-microwell bottom portion, and each sub-microwell may taper in cross-sectional area going from the sub-microwell top portion to the sub-microwell bottom portion. For example, each each sub-microwell may be frustoconical or frustopyramidal.

Each microwell may comprise a microwell top portion and a microwell bottom portion, and each microwell may taper in cross-sectional area going from the microwell top portion to the microwell bottom portion. For example, each microwell may be frustoconical or frustopyramidal.

The sub-microwells, microwells, and well may be integrally formed.

The cell culture device may comprise a magnetic or magnetizable member positioned below the sub-microwells. The magnetizable member may be a wire grid. The well may be defined at least in part by a well bottom wall, and the wire grid may be embedded within the well bottom wall.

Each microwell may have a microwell top portion and an opposed microwell bottom portion, and the top portion of each microwell may have a microwell width of at least 100 microns. Each microwell may have a microwell depth between the top portion and the bottom portion of at least 75 microns.

Each microwell may have a microwell top portion and a microwell bottom portion. Each microwell may comprise a largest dimension at the microwell top portion, and a microwell depth between the microwell top portion and the microwell bottom portion. The ratio of the largest dimension to the microwell depth may be between 1.1:1 and 1.9:1.

According to another microwell aspect, a cell culture device comprises a well. A plurality of microwells are within the well. Each comprises a microwell top portion and a microwell bottom portion. Each microwell comprises a largest dimension at the microwell top portion, and a microwell depth between the microwell top portion and the microwell bottom portion. The ratio of the largest dimension to the microwell depth is between about 1.1:1 and 1.9:1.

The largest dimension may be at least 140 microns. The microwell depth may be at least 75 microns.

Each microwell may taper in cross-sectional area going from the microwell top portion to the microwell bottom portion. For example, each microwell may be frustoconical or frustopyramidal.

The well may be defined at least in part by at least one well sidewall, and a well bottom wall. The well bottom wall may be transparent or translucent. Each microwell may be defined at least in part by at least one microwell sidewall extending upwardly from the well bottom wall.

The cell culture device may further comprise a magnetic or magnetizable grid positioned below the microwells. The well may be defined at least in part by a well bottom wall, and the grid may be embedded within the well bottom wall.

The microwells and well may be integrally formed.

The cell culture device may further comprise a first common fluid volume within the well above the microwells.

The cell culture device may further comprise a set of sub-microwells within each microwell. Each set of sub-microwells may comprise four sub-microwells arranged in a 2×2 array.

The well may be defined at least in part by at least one well sidewall, and a well bottom wall. Each microwell may be defined at least in part by at least one microwell sidewall extending upwardly from the well bottom wall. Each sub-microwell may be defined at least in part by at least one sub-microwell sidewall extending upwardly from the well bottom wall. Each sub-microwell may be further defined by a portion of one of the microwell sidewalls.

Each sub-microwell may comprise a sub-microwell top portion and a sub-microwell bottom portion, and each sub-microwell may taper in cross-sectional area going from the sub-microwell top portion to the sub-microwell bottom portion. For example, each sub-microwell may be frustoconical or frustopyramidal.

The sub-microwells may be integrally formed with the microwells and well.

The cell culture device may further comprise a second common fluid volume within each microwell above the set of sub-microwells.

Any feature or combination of features described herein are included provided that the features included in any such combination are not mutually inconsistent as will be apparent from the context, this specification, and the knowledge of one of ordinary skill in the art.

DRAWINGS

Reference is made in the detailed description to the accompanying drawings, in which.

DETAILED DESCRIPTION

Figure 1:
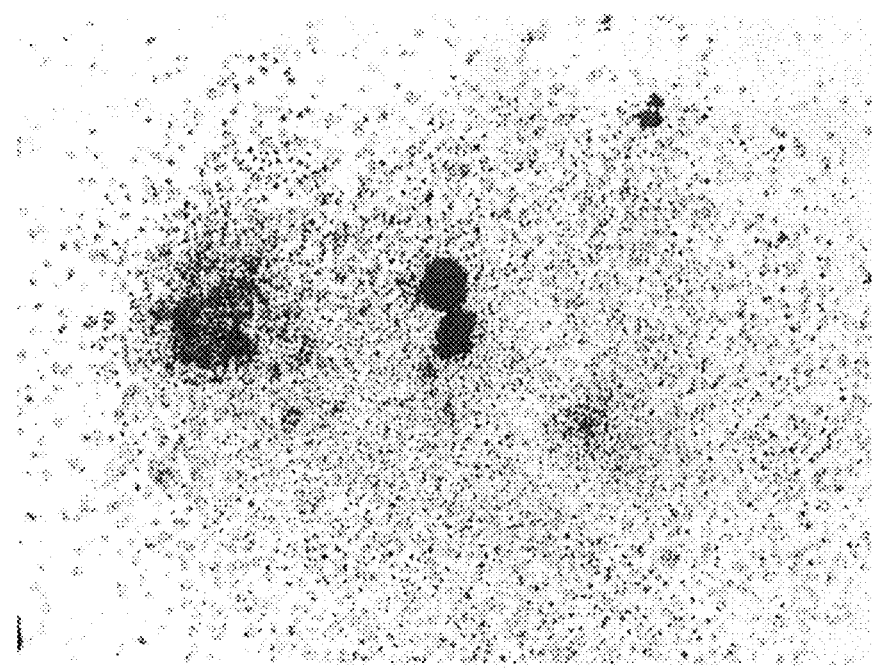
FIG. 1A is an image of colonies typically observed in hematopoietic colony assays, showing a number of individual colonies with a large degree of overlap.
FIG. 1B is an image of colonies typically observed in hematopoietic colony assays, showing one colony with multiple centers, derived from a single progenitor.
Figure 1:
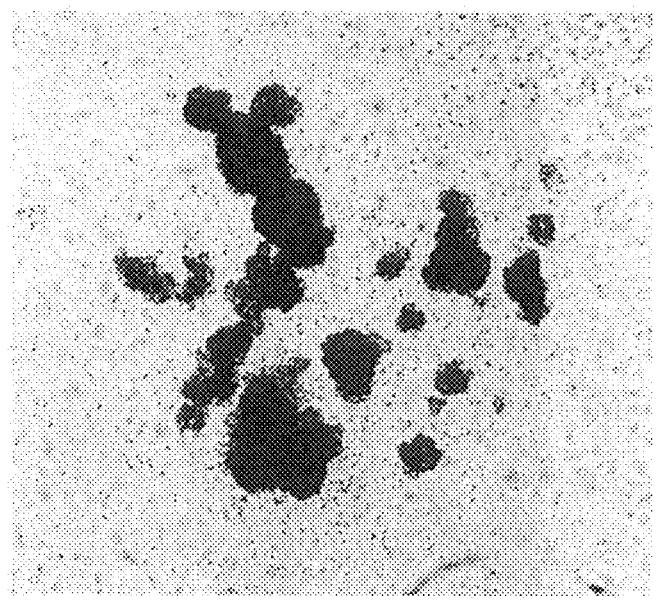

Various apparatuses or processes will be described below to provide an example of an embodiment of each claimed invention. No embodiment described below limits any claimed invention and any claimed invention may cover processes or apparatuses that are not described below. The claimed inventions are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any invention disclosed in an apparatus or process described below and for which an exclusive right is not granted by issuance of this patent application may be the subject matter of another protective instrument, for example, a continuing patent application, and the applicants, inventors or owners do not intend to abandon, disclaim or dedicate to the public any such invention by its disclosure in this document.

Semisolid media may present some limitations to CFC assays for quantification or sub-cloning of individual cells. Since cells are not firmly fixed in the medium, colonies may be disturbed by handling of the cultureware. For example, disturbances such as frequent movement of culture dishes or addition of liquid reagents to the culture is likely to disturb the colonies. This may limit the type and number of manipulations that can be conducted on such cultures.

In addition, since there are no physical boundaries within the cultures, some colonies may overlap, making it difficult to determine if neighboring groups of cells are colonies derived from individual progenitor cells, or represent a single colony with multiple centers arising from daughter cells that have migrated a short distance from the original progenitor cell. This can lead to erroneous counts of total colony number.

Further, the morphological characteristics of colonies of different mature cell lineages are often insufficiently distinct, making classification these colonies a subjective process prone to a high degree of variability. In the case of CFC assays of hematopoietic progenitors for example, it can be difficult to distinguish colonies derived from granulocyte, monocyte, and megakaryocyte progenitors, allowing for reliable differentiation of only major lineage classes (erythroid and myeloid). In order to reliably classify colonies according to the type of progenitor cell from which it was derived, specific labeling and staining methods may be required. Such methods frequently rely on introducing probe molecules that recognize specific cell surface markers or intracellular components. Staining methodologies typically involve fixation of the cells and a sequence of subsequent wash, stain, and destain procedures. These methods are not compatible with colony assays of non-adherent cells in semi-solid media, since colonies are disrupted by the addition of the fixing, staining and washing solutions.

An additional limitation of standard CFC assays in semi-solid media is the occurrence of multiple colonies in close proximity to another, or colonies with overlapping boundaries, as shown in FIG. 1A. Such colonies can be difficult to distinguish from multi-centric colonies derived from a single cell, as shown in FIG. 1B. This not only results in a highly subjective analysis of colony enumeration, but also complicates the extraction of individual colonies from the culture for further expansion or sub-cloning due to the presence of extraneous cells from neighbouring colonies.

Although the use of known microwell devices overcomes some of the drawbacks noted above, in known microwell devices, colonies often spread beyond the volume of the microwells. This results in spreading into adjacent microwells, and/or the washing out of cells in the colonies during routine handling. Further, in known microwell devices, it is common for more than one progenitor cell to be seeded into each microwell, thus resulting in the growth of more than one colony in each microwell. This can lead to error when counting colonies.

The present disclosure relates to cell culture devices that include microwells. The cell culture devices may be used for colony forming assays, and may overcome some or all of the drawbacks noted above. Particularly, as will be described in further detail below, cell culture devices as described herein may better compartmentalize individual colonies, may better contain the colonies as they grow such that they do not exceed volume of the microwell, and may result in robust entrapment of multi-cell colonies over multiple days of culture, in order to prevent or reduce the chance of their dispersal or spreading between microwells during manipulations such as addition or removal of solutions. This may allow the cell culture devices to be used for simple, quantitative colony forming assays lasting from about 4 to 20 days. Further, this may segregate colonies from their nearest neighbours and reduce the occurrence of overlapping cells to enable objective enumeration of colonies and extraction of individual colonies without contamination of unrelated cells.

In addition, cell culture devices as described herein may effectively immobilize the cells, thereby eliminating the need for fixation of the specimen prior to staining. This may enable sensitive live cell staining methods (e.g. staining of colonies for reliable classification of colony types) that do not alter the metabolic and physical characteristics of the cells. In combination with specific cell staining methods, colonies in the microwells can be classified into sub-types (e.g. for hematopoietic colonies: erythroid, myeloid, granulocyte, megakaryocyte, monocyte etc.). Further, the cell culture devices described herein permit imaging of cells.

Figure 2:
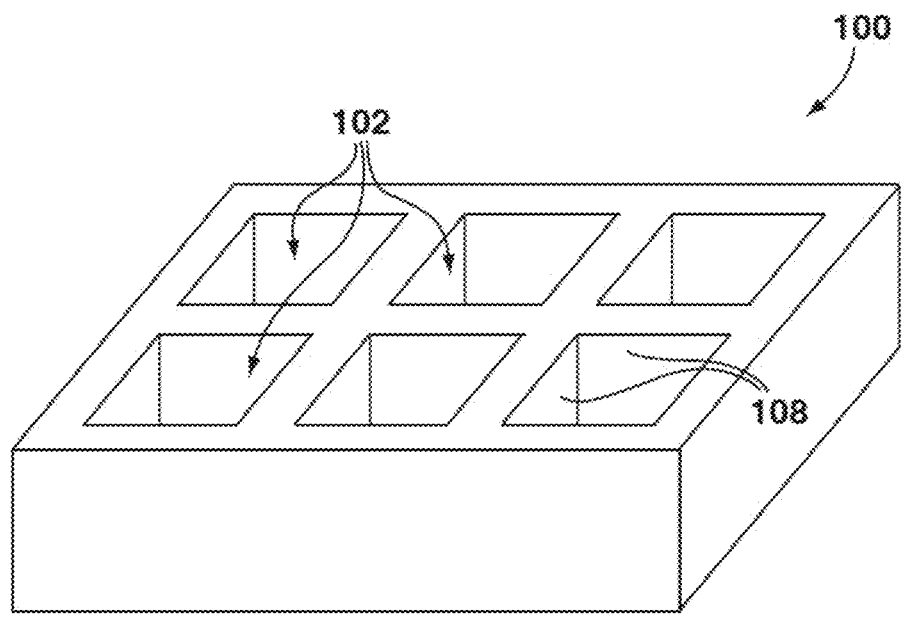
FIG. 2 is a perspective view of an exemplary cell culture device of the present disclosure.
Figure 3:
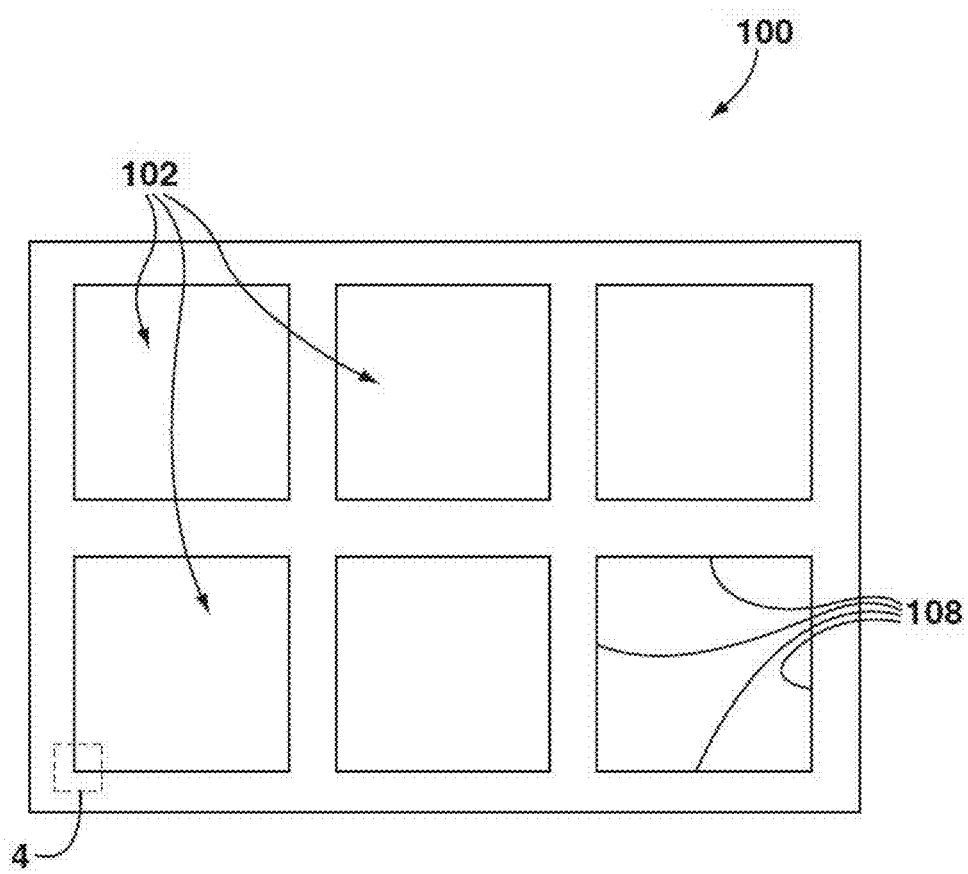
FIG. 3 is a top plan view of the cell culture device of FIG. 2.

Referring to FIGS. 2 and 3, an exemplary cell culture device 100 is shown. The cell culture device 100 includes at least one well 102. As used herein, the term "well" refers generally to any fluid reservoir in which cells in a liquid media may be deposited for the culture of the cells. In the example shown, the cell culture device 100 is in the form of a multi-well plate, and includes six wells 102. In alternate examples, a cell culture device in the form of a multi-well plate may include an alternate number of wells, such as 24 or 96 wells. The wells of multiwell plates are typically circular in cross-section rather than rectangular as shown in FIG. 2. However, any vessel with a general planar bottom is acceptable. In further alternate examples, a cell culture device may in another suitable form, such as cell culture dish (as used in the Examples section hereinbelow). In such an example, the cell culture device may include only one well (i.e. the single fluid reservoir of the cell culture dish).

Figure 5:
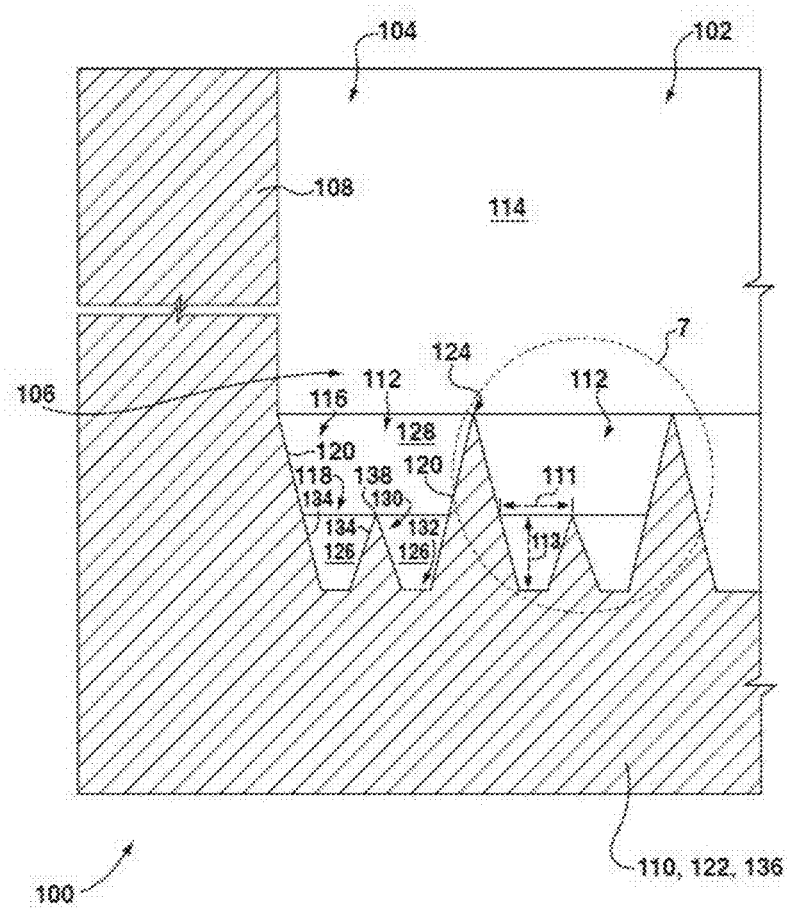
FIG. 5 is a cross section taken along line 5-5 in FIG. 4.

Referring to FIGS. 2 and 5, each well 102 includes a well top portion 104 and a well bottom portion 106. Further, each well 102 is defined by at least one well sidewall 108, and a well bottom wall 110.

The wells may be of any suitable shape. In the example shown, the wells 102 are generally square, and are defined by four well sidewalls 108, and the well bottom wall 110. Further, the wells may be of any suitable size. For example, the wells may have a volume of between about 30 μL and about 10 L. For example, the low end of the range for one well of a 384-well plate, is about 30 μL and the high end of the range for a typical 6-well plate is about 100 mL. For a QTRAY, the volume is about 1.1 L and for a plate that fills the footprint of a standard incubator shelf, the volume can be as high as 10 L. According, in one embodiment, the wells have a volume between about 30 μL and about 10 L. In another embodiment, the wells have a volume between about 30 μL and 100 mL. In yet another embodiment, the wells have a volume between about 30 μL and about 6 mL.

Figure 4:
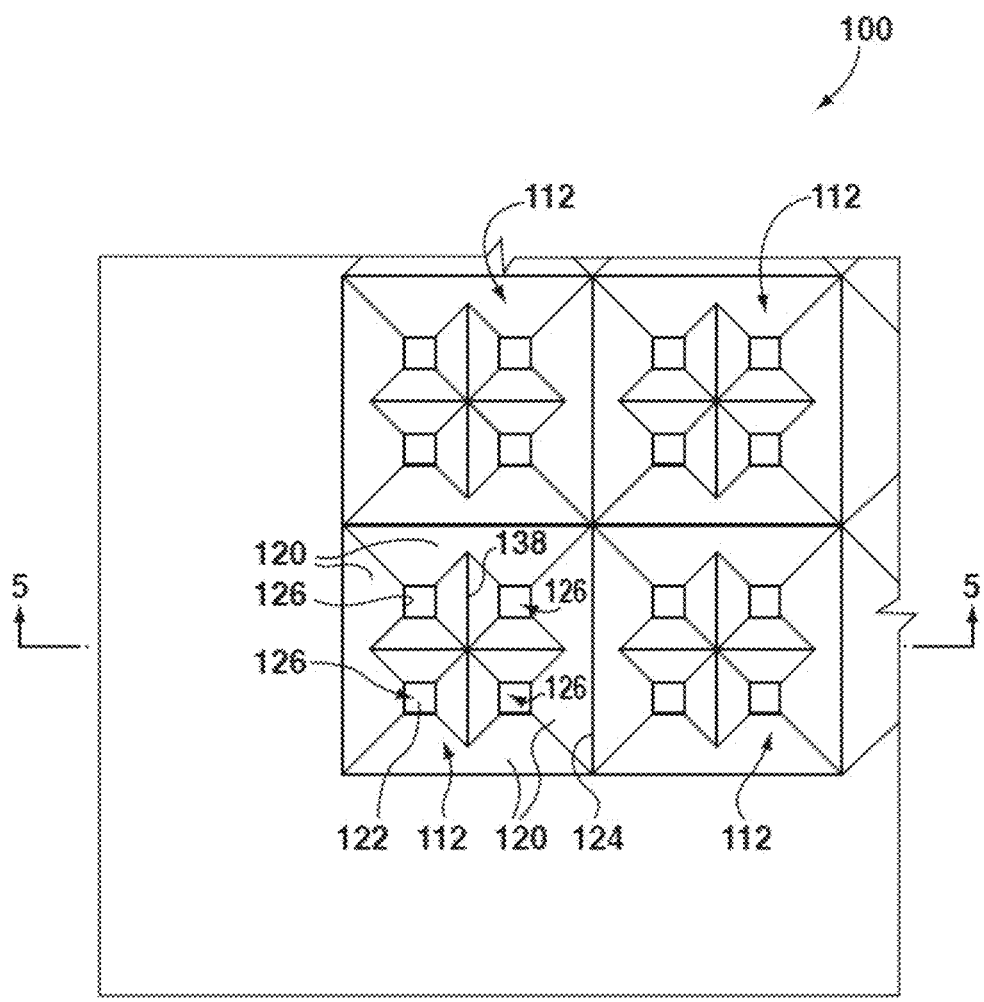
FIG. 4 is an enlarged view of the region shown in box 4 in FIG. 3.
Figure 6:
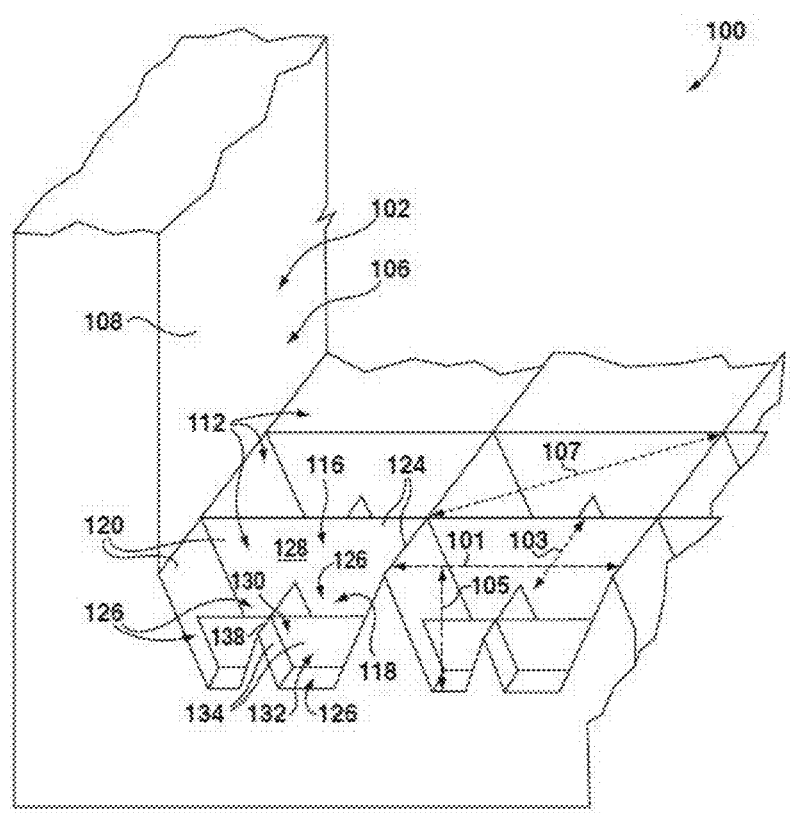
FIG. 6 is a perspective cut-away view of the region shown in box 4 in FIG. 3.

Referring now to FIGS. 4 to 6, within each well 102 is a plurality of microwells 112, and a first common fluid volume 114 (shown in FIG. 5) above the microwells 112. Specifically, the microwells 112 are at the well bottom portion 106 of each well, and are spaced from the well top portion 104. The space at the well top portion 104 of each well 102 forms the first common fluid volume 114, which is in communication with each of the microwells 112.

The microwells 112 provide a volume within which individual progenitor cells may seed and grow into colonies. That is, a liquid media containing progenitor cells may be deposited into each well 102. The cell culture device 100 may then be centrifuged, so that the progenitor cells are forced to the well bottom portion 106 of each well 102 and into the microwells 112, so that the individual cells are separated into the microwells 112 and may grow to form colonies. Alternately, the cells may settle into the microwells 112 under the force of gravity. The first common fluid volume 114 allows for each microwell 112 within a given well 102 to share a common media, so that the cells within the microwells 112 are cultured under generally the same conditions.

Referring to FIGS. 5 and 6, each microwell 112 comprises a microwell top portion 116 and a microwell bottom portion 118. Each microwell 112 is defined by at least one microwell sidewall 120 extending between the microwell top portion 116 and the microwell bottom portion 118, and a microwell bottom surface 122 at the microwell bottom portion.

Referring to FIG. 5, in the example shown, the microwell bottom surface 122 of each microwell 112 within a given well 102 is formed by the well bottom wall 110 of the given well 102. Further, the microwell sidewalls 120 extend integrally upwardly from the well bottom wall 110, and the microwell sidewalls 120 of the microwells 112 that are adjacent the well sidewall 108 are integrally formed with the well sidewall 108.

In alternate examples, the well bottom walls and well sidewalls may be separately formed from the microwell bottom surfaces and microwell sidewalls. For example, the microwells may be formed as an insert that is seated on and optionally secured to the bottom wall of a well (as described in the Examples section hereinbelow).

The microwells may be of any suitable shape. Referring to FIG. 4, in the example shown, each microwell 112 is generally square at the microwell top portion 116, and is defined by four microwell sidewalls 120. Further, referring to FIGS. 5 and 6, each microwell 112 tapers in cross-sectional area going from the microwell top portion 116 to the microwell bottom portion 118. More specifically, in the example shown, each microwell 112 is generally frustopyramidal. This shape generally encourages progenitor cells to seed within the microwells 112, rather than between adjacent microwells 112. More specifically, in the example shown, as the microwells 112 are generally frustopyramidal, the microwell sidewalls 120 of adjacent microwells 112 meet at an apex 124, so that cells generally may not seed between the microwells 112.

In examples wherein the microwells 112 taper in cross-section going from the microwell top portion 116 to the microwell bottom portion 118, the angle of the microwell sidewalls 120 with respect to the vertical (also referred to herein as the "wall angle") may be any suitable angle. In some examples, the angle may be less than about 30 degrees, for example between 10 degrees and 20 degrees. In other examples, the angle may be as low as 2 degrees. As shown in the Examples section hereinbelow, as the wall angle decreases, the volume of the microwell increases, which results in improved containment of cell colonies.

In the example shown, the microwell sidewalls 120 extend at a uniform angle from the microwell top portion 116 to the microwell bottom portion 118. In alternate examples (not shown), the microwell sidewalls may include a first portion that extends downwardly from the microwell top portion at a first angle, and a second portion that extends downwardly from the first portion at a second angle. The second angle may be less than the first angle (e.g. the second angle may be 0 degrees). This may allow for the microwell sidewalls of adjacent microwells meet at an apex, while still allowing for the microwell bottom surface to be relatively large, and the volume of the microwell to be relatively large.

In alternate examples (not shown), each microwell may be generally circular at the microwell top portion, and may be generally frustoconical. In yet further alternate examples, each microwell may be another suitable shape at the microwell top portion, such as triangular, rectangular, trapezoidal, or hexagonal.

In the example shown, the microwells 112 within a given well 102 are generally of the same shape and size. In alternate examples (not shown), the microwells within a given well may have different shapes and sizes.

In the example shown, each microwell 112 has a generally central axis of symmetry. In alternate examples (not shown), one or more of the microwells may be without a central axis of symmetry.

In general, colonies formed in microwells may have an average size of between about 10 and 100,000 cells; however, some colonies may grow to have more than 1 million cells or. Cell colonies of 1 million cells would be expected to have a volume of approximately 1.0 µL. Since the microwells in known microwell devices are not generally intended for cell culture, for the most part they are not sized to accommodate the occasional large colonies that occur. However, in one known microwell device, the microwells have a volume of about 0.1 µL or more (Ungrin WO 2008/106,771 which may accommodate these large colonies. As noted hereinabove, in these microwell devices, cells still tend to spread beyond the volume of the microwells. Surprisingly, it has presently been determined that by dimensioning the microwells such that the ratio of their largest dimension at the top portion to their depth (also referred to hereinafter as the "aspect ratio") is less than 1.9:1, and more particularly, between 1.9:1 and 1.1 to 1, the spread of cells beyond the microwells may be reduced, and immobilization of larger colonies may be achieved.

For example, referring to FIG. 6, each microwell 112 is generally square at the microwell top portion 116, and has a microwell width 101 and a microwell length 103 at the top portion 116, and a microwell depth 105 between the microwell top portion 116 and the microwell bottom portion 118. As the microwells 112 are generally square at the top portion 116, the largest dimension across the top portion is diagonal line 107. Accordingly, if the microwell depth 105 is approximately 1 mm, in order to have an aspect ratio of less than 1.9:1, the length of line 107 will be less than 1.9 mm. For example, the microwell width 101 may be 1 mm, and the microwell length 103 may be 1 mm, so that the length of line 113 is approximately 1.4.

In alternate examples, the microwell width, microwell length, and microwell depth may be another size. For example, the microwell width and microwell length may generally be 100 microns or greater, and more specifically 500 microns or greater, and the microwell depth may generally be 75 microns or greater. In an example wherein the microwells are square at the top portion and have a microwell width and microwell length of 500 microns at the top portion, the largest dimension at the top portion would be approximately 707 microns. In such examples, in order to have an aspect ratio of less than 1.9:1, the microwell depth will be greater than approximately 372 microns.

In alternate examples (not shown), wherein the microwells are of a different shape, the largest dimension across the top portion may be another dimension. For example, if the microwells are circular at the top portion, the largest dimension would be the diameter at the top portion.

The density and total number of the microwells within each well may vary depending on the size and shape of the microwells and the size and shape of the wells. In some examples, the density of the microwells within each well may be between 0.5 and 4.0 microwells per square millimeter. In one particular example, each well may include about 960 microwells.

Referring still to FIGS. 4 to 6, in the example shown, within each microwell 112 is a set of sub-microwells 126, and a second common fluid volume 128 within each microwell 112 above the set of sub-microwells 126.

As noted hereinabove, in known microwell devices, it is common for more than one progenitor cell to be seeded into each microwell, thus resulting in the growth of more than one colony in each microwell. By providing a set of sub-microwells 126 in each microwell 112, even if more than one progenitor cell is seeded into each microwell 112, the progenitor cells will generally separate into adjacent sub-microwells 126 and grow separate colonies.

Further, as will be described in more detail hereinbelow, the sub-microwells 126 may be sized to house an average colony (e.g. a colony of up to 100,000 cells), as opposed to a large colony. Accordingly, the sub-microwells 126 will be of a sufficient size to house the majority of cell colonies that grow; however, if a large colony does grow in a sub-microwell 126, the large colony may grow into the second common fluid volume 128 and will be contained within the microwell 112 housing the sub-microwell 126.

In addition, by providing sub-microwells 126 within each well 112, the cells from small colonies may be concentrated at the microwell bottom surface 122. This may enhance the ability to detect small colonies by brightfield microscopy. This, for example, could enable more rapid colony assays by detecting colonies at an earlier timepoint or to detect progenitors with lower proliferative potential.

Referring to FIGS. 5 and 6, each sub-microwell 126 comprises a sub-microwell top portion 130 and a sub-microwell bottom portion 132. Further, each sub-microwell 126 is defined by at least one sub-microwell sidewall 134 extending between the sub-microwell top portion 130 and the sub-microwell bottom portion 132, and a sub-microwell bottom surface 136 at the sub-microwell bottom portion 132.

The sub-microwells 126 may be of any suitable shape. In the example shown, each sub-microwell 126 is generally square at the sub-microwell top portion 130, and is defined by four sub-microwell sidewalls 134.

Referring to FIG. 5, in the example shown, the sub-microwell bottom surface 136 of each sub-microwell 126 within a given well 102 is formed by the well bottom wall 110 of the given well 102. Further, of the four sub-microwell sidewalls 134 of each sub-microwell 126, two are formed by a portion of the microwell sidewalls 120, and another two extend integrally upwardly from the well bottom wall 110.

In alternate examples (not shown), any of the microwell bottom walls, microwell sidewalls, sub-microwell bottom surfaces and sub-microwell sidewalls may be formed from separate pieces of material. For example, a given set of sub-microwells may be formed as an insert that is seated on the microwell bottom surface of one of the microwells.

Referring still to FIGS. 5 and 6, each sub-microwell 126 tapers in cross-section going from the sub-microwell top portion 130 to the sub-microwell bottom portion 132. More specifically, in the example shown, each sub-microwell 126 is generally frustopyramidal. Similarly to the microwells 112, this configuration encourages progenitor cells to seed within the sub-microwells 126, rather than between adjacent sub-microwells 126. More specifically, in the example shown, where the sub-microwells 126 are generally frustopyramidal, the sub-microwell sidewalls 134 of adjacent sub-microwells 126 meet at an apex 138, so that cells generally may not seed between the sub-microwells 126.

In alternate examples (not shown), each sub-microwell may be generally circular at the sub-microwell top portion, and may be generally frustoconical. In yet further alternate examples, each sub-microwell may be another suitable shape at the sub-microwell top portion, such as triangular, rectangular, trapezoidal, or hexagonal.

In examples wherein the sub-microwells taper in cross-section going from the sub-microwell top portion to the sub-microwell bottom portion, the angle of the sub-microwell sidewalls with respect to the vertical may be any suitable angle. In some examples, the angle may be less than about 30 degrees, for example between 10 degrees and 20 degrees. In other examples, the angle may be as low as 2 degrees.

As mentioned hereinabove, the sub-microwells 126 may be sized to house an average colony. For example, the sub-microwells may have a volume of between about $3\times10^{-6}$ µL and about 1.0 µL. For example, referring to FIG. 5, the sub-microwells 126 may have a width at the top portion of between about 30 µm and 1 mm, and a depth 113 between the top portion and the bottom portion of between about 30 µm and 1 mm. Further, the sub-microwell sidewalls 134 may extend at an angle of between about 1 and 37 degrees from the vertical.

Each microwell 112 may include any suitable number and arrangement of sub-microwells 126. In the example shown, each microwell 112 includes 4 sub-microwells 126, which are arranged in a 2×2 array. In alternate examples, the sub-microwells may be arranged in another configuration, such as a 2×1, 3×1, 3×2, 3×3 or larger array.

Referring still to FIGS. 5 and 6, the well bottom walls 110, which also form the microwell bottom surfaces 122 and the sub-microwell bottom surfaces 136, may be translucent or transparent. This may allow for the viewing of the cell colonies within the cell culture device 100, for example by microscopy or other visual imaging methods. In the example shown, the sub-microwell bottom surface 136 is generally flat, and each sub-microwell bottom surface 136 is generally co-planar. This may aid in viewing of the cell colonies under microscopy. However, in alternate examples (not shown), the sub-microwell bottom surfaces may be another shape, for example rounded. In further alternate examples (not shown), the sub-microwells may not include a sub-microwell bottom surface. For example, the sub-microwell sidewalls may meet at an apex.

In some examples (not shown), the microwell bottom surfaces and/or the sub-microwell bottom surfaces may include demarcations as an index to identify the location of the microwells or sub-microwells within the cell-culture device.

In further examples (not shown), the interior surfaces of the cell culture device may be coated with a hydrophobic coating. The hydrophobic coating may minimize or reduce the formation of a meniscus when a liquid is placed in the cell culture device, which may promote even distribution of a sample placed into the cell culture device.

In further examples (not shown), the interior surfaces of the cell culture device may be treated to promote wetting so that the microwells and sub-microwells are more easily filled with liquid.

As mentioned hereinabove, in some examples, cells may be seeded into the microwells 112 and sub-microwells 126 by centrifugation or by gravity. In alternate examples, magnetic forces may be used to seed the cells into the microwells 112 and sub-microwells 126. For example, in use, the cells may be labelled with magnetic particles, such as EASYSEP particles or other magnetic particles. Specific cell types of interest can be coupled to magnetic particles using antibody cocktails specific for cell surface markers on the target cells as well as an active moiety on the carrier particles, such as dextran. With such cocktails, antibody complexes are formed that crosslink the target cells to the magnetic particles to form a mixture of suspended magnetic particles, magnetic particle and target cell complexes, and unbound non-targeted cells. A suspension of the cells may then be deposited into the wells 102, and may be subjected to a magnetic field gradient in the direction of the well bottom walls 110. The particles will move in the direction of the gradient and collect in the sub-microwell bottom portions 132. The unwanted cells remaining in suspension can be washed out of the wells 102, so that only the target cells remain to form colonies during subsequent incubation.

Figure 7:
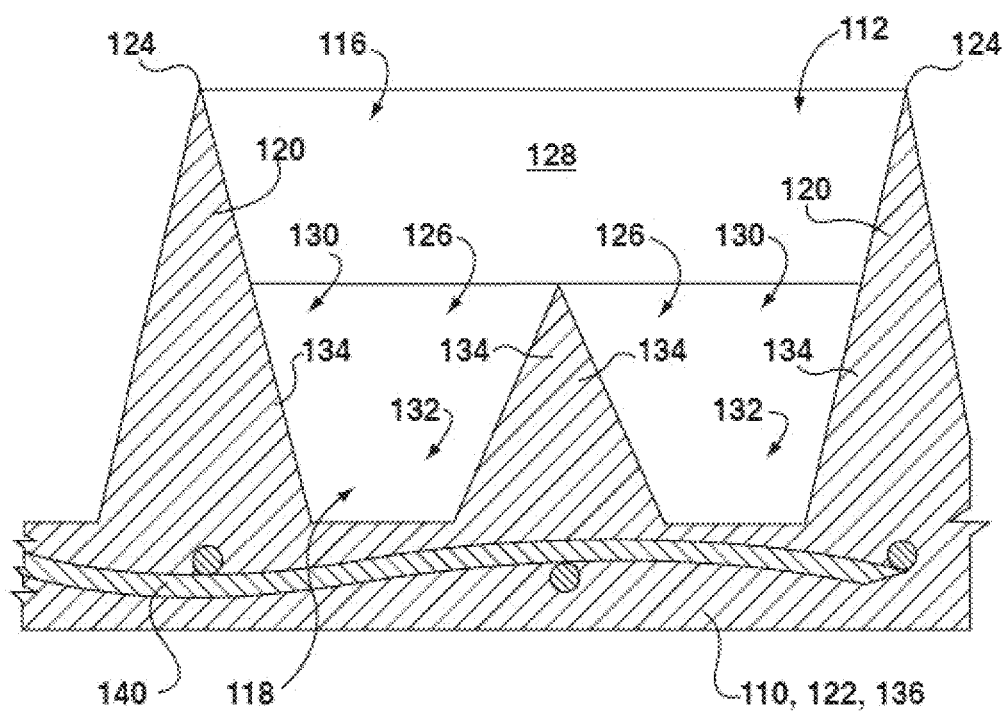
FIG. 7 is an enlarged view of the region shown in circle 7 in FIG. 5, showing a magnetizable grid embedded in the well bottom portion.

Referring now to FIG. 7, in some examples, a cell culture device may include a magnetic or magnetizable member positioned below the sub-microwells, in order to increase the magnetic field gradient, and enhance the speed at which the particles collect in the sub-microwell-bottom portions. In the example shown, the magnetizable member includes a magnetizable wire grid 140, which is embedded in the well bottom wall 110. The magnetic field gradient may magnetize the wire grid 140, and increase the magnetic field gradient.

In alternate examples (not shown) the wire grid may be configured to attract the magnetically labelled elements to a specific location within each well.

EXAMPLES

Example 1

Production of Cell Culture Devices

Cell culture devices as described above were prepared by fabricating the microwells as an insert, and inserting them into a culture dish. Some of the microwells included sub-microwells, and some did not. The microwells were prepared to have various aspect ratios, as described above.

A negative mold of several microwell configurations was produced by CNC machining of a solid aluminum disc. These circular molds have a diameter of 35 mm, a thickness of 20 mm, and exhibit a surface with the inverse topology the microwells. The microwell inserts were produced by casting a polydimethylsiloxane-based (PDMS) elastomer into the mold with subsequent curing of the elastomer to form a flexible disc containing the microwells. Specifically, the elastomer was prepared from a 10:1 (w/w) homogeneous mixture of SYLGARD 184 (DOW CORNING) elastomer and curing agent. This mixture of silicone components was exposed to a vacuum (<10 mTorr, 1 hr) to remove any volatile components prior to casting into the aluminum molds. 1.5 g to 1.7 g of the elastomer was slowly poured onto the mold surface and allowed to spread to form a layer of uniform thickness over the mold. The base of the mold was then placed on a hot plate heated to 180° C. Due to the minimal thickness of the mold and high conductivity of the aluminum material, rapid heat transfer to the mold surface resulted in rapid curing of the silicone elastomer. After heating for a period of 5 min, the mold was removed from the hot plate and cooled to ambient temperature by briefly placing on an aluminum plate cooled to 0° C. The hardened PDMS gel was demolded by gently pulling up on one edge of the casting to remove the disc containing the microwells.

The microwell inserts were sterilized by dry heat (135° C. for 1 hr) prior to insertion into 35 mm culture dishes (BECTON-DICKINSON, 35-1008). The microwell inserts were bonded into the dishes by placing a 125 uL droplet of the above SYLGARD elastomer and curing agent mix into the center of the dishes and then aseptically inserting the microwell inserts into the dishes with the array surface facing up. The inserts were sealed into wells by incubating (2 to 4 hrs) the dishes with the array inserts in an oven at 80-85° C. to heat cure the bonding layer of SYLGARD.

Figure 8:
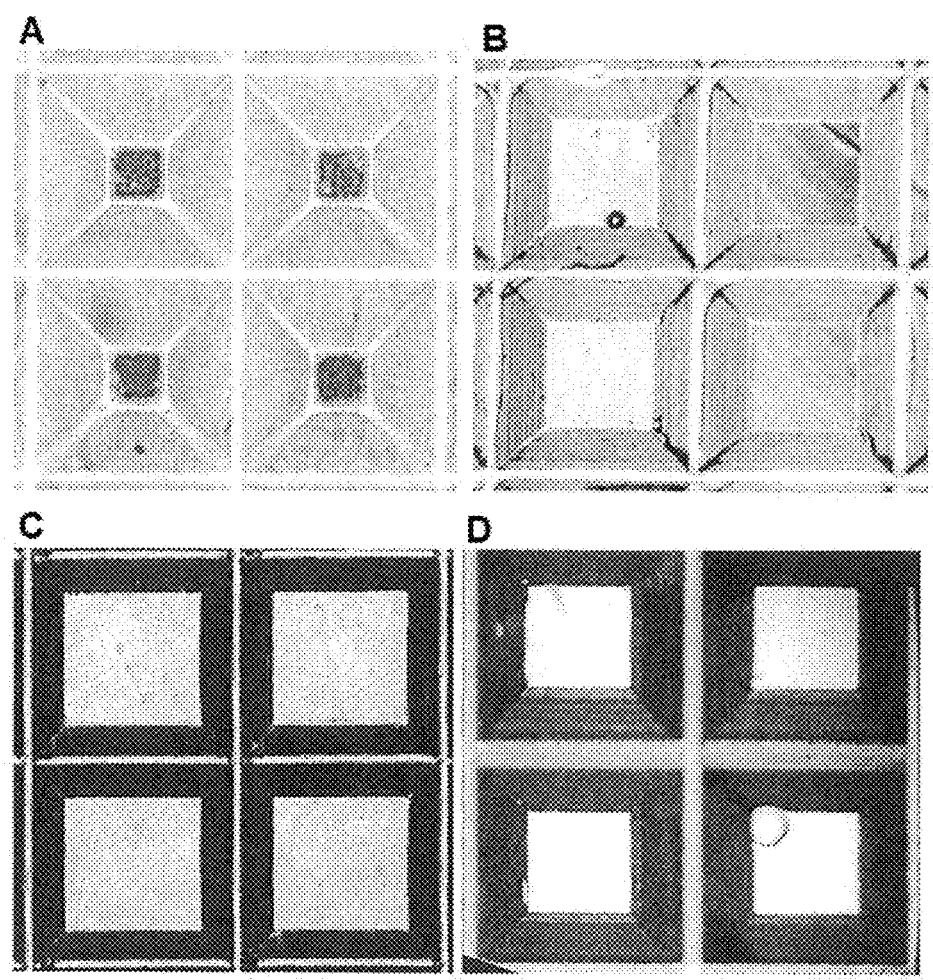
FIG. 8 shows images of various microwell configurations acquired by brightfield microscopy.
Figure 8:
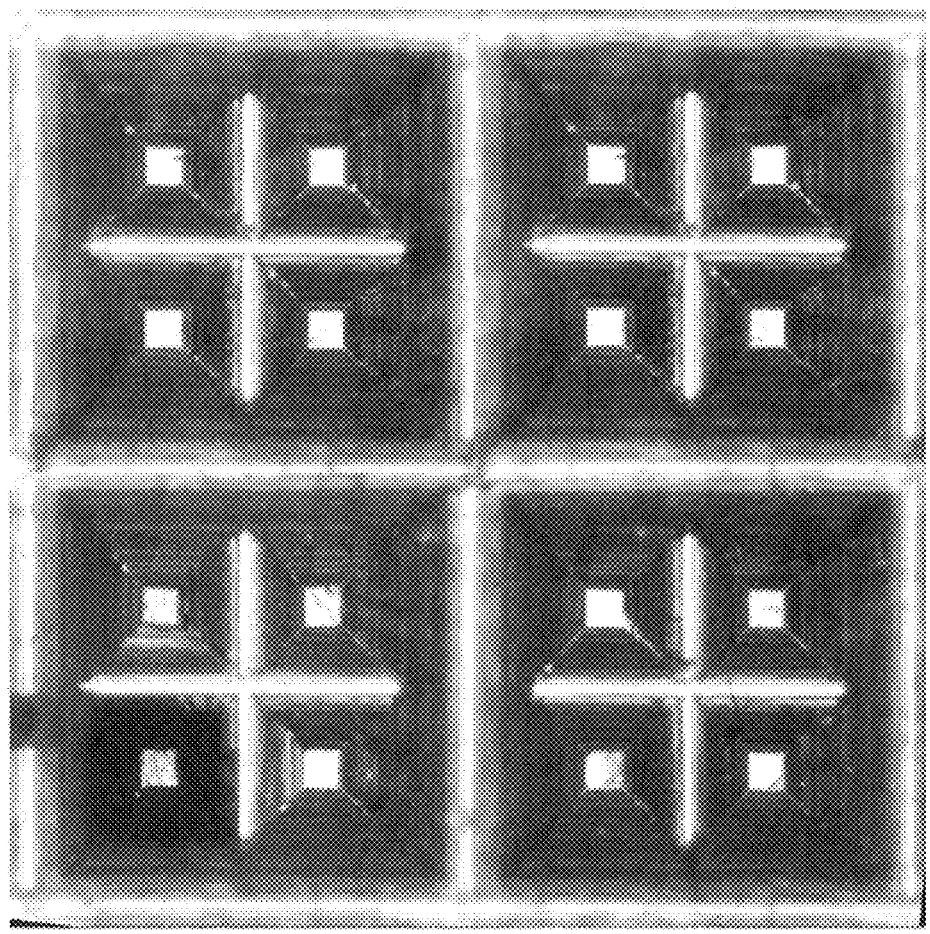

Examples of some of the microwell arrays produced in this manner are shown in FIG. 8, which are top view images of the microwells of the inserts acquired by brightfield microscopy. The dimensions of the microwells are shown in the following table, with aspect ratio shown as maximum horizontal dimension to depth:

| Configuration | Wall angle (degrees) | Microwell width (mm) | Microwell depth (mm) | Aspect ratio |
| --- | --- | --- | --- | --- |
| A | 37 | 0.8 | 0.38 | 3.0:1 |
| B | 20 | 0.8 | 0.5 | 2.3:1 |
| C | 15 | 0.8 | 0.5 | 2.3:1 |
| D | 15 | 1.0 | 1.0 | 1.4:1 |

Example 2

Effect of Well Configuration on Immobilization of Particles

Cell culture devices having microwells of varying dimensions were evaluated for their ability to compartmentalize particles. The cell culture devices tested in this example did not contain sub-microwells. The evaluation was done using fluorescent polystyrene microparticles (Bangs FS06F, 7.3 um diameter). A suspension of microparticles was placed into a few individual microwells of several cell culture devices. All microwells were square at the microwell top portion. The microwells had the following dimensions:

| Configuration | Wall angle (degrees) | Microwell width (mm) | Microwell depth (mm) | Aspect ratio |
| --- | --- | --- | --- | --- |
| A | 15 | 1.0 | 1.0 | 1.4:1 |
| B | 15 | 0.8 | 0.5 | 2.3:1 |
| C | 37 | 0.8 | 0.38 | 3.0:1 |

The particles were allowed to settle into wells by gravity; the remaining wells were left empty, containing only phosphate buffer (PBS). The cell culture devices were then subjected to methods of physical disturbance representative of manipulations typical for cell culture applications. Specifically, a wash procedure was performed by removing the overlying PBS and replacing with a 2.0 mL volume of fresh PBS. The cell culture devices were then subjected to rapid lateral (side-to-side) movement. Microwells surrounding the particle-containing wells were observed for evidence of well-well spread of particles and imaged by fluorescence microscopy (LEICA DMIL inverted microscope, 4x objective lens). Images of the wells surrounding the particle containing wells are shown in FIG. 9.

Figure 9:
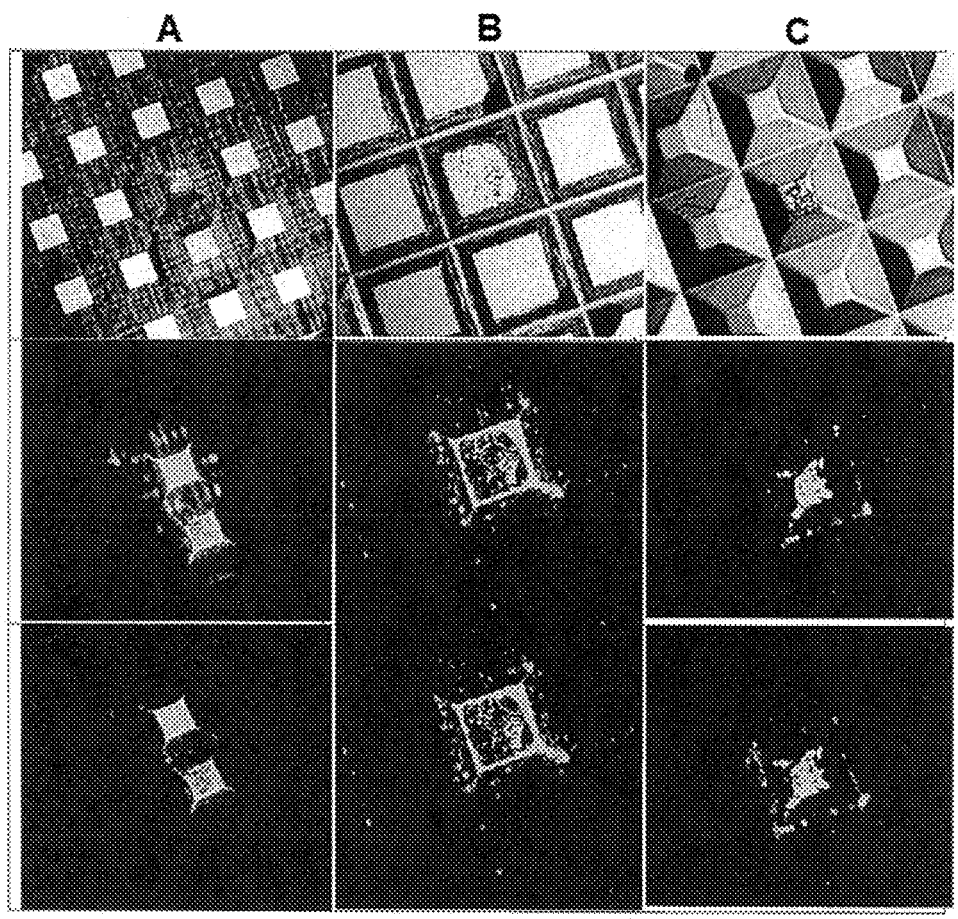
FIGS. 9A to 9C are images showing the immobilization of fluorescent beads in microwells.

In FIG. 9, the first image in each column is a brightfield view of a microwells after placement of fluorescent beads in microwells near the center of the cell culture device. The next image in each column shows the fluorescence of observed in the microwells prior to any manipulation of the cell culture device. The last image in each column is shows the fluorescence observed in the microwells after washing and physical movement of the cell culture devices.

No evidence of transfer of particles is seen after manipulation in the images obtained using fluorescence microscopy. This shows that microwells with an aspect ratio of 1.4:1 to 3.0:1 are effective in restricting movement of small particles during routine cell culture operations.

Example 3

Effect of Well Configuration on Containment of Cell Colonies

Human hematopoietic progenitor cells in liquid medium were inoculated into cell culture dishes containing microwells of various configurations. The cell culture devices tested in this example did not contain sub-microwells. All microwells were square at the microwell top portion. The dimensions of the microwells are outlined in the table below:

| Configuration | Wall angle (degrees) | Microwell width (mm) | Microwell depth (mm) | Aspect ratio |
| --- | --- | --- | --- | --- |
| A | 37 | 0.8 | 0.38 | 3.0:1 |
| B | 30 | 1 | 0.75 | 1.9:1 |
| C | 20 | 1 | 0.75 | 1.9:1 |
| D | 15 | 1 | 0.75 | 1.9:1 |
| E | 15 | 1 | 1 | 1.4:1 |

The cell culture devices were inoculated with a colony density of approximately 7 colonies/cm$^2$ and cells were sedimented into the microwells by slow speed centrifugations. The inoculated cell culture devices were subsequently incubated in a permissive culture environment of 37° C. and a humidified atmosphere containing 5% $CO_2$. Colony formation was monitored at two day intervals and any evidence of microwell to microwell spread of cells was noted.

Figure 10:
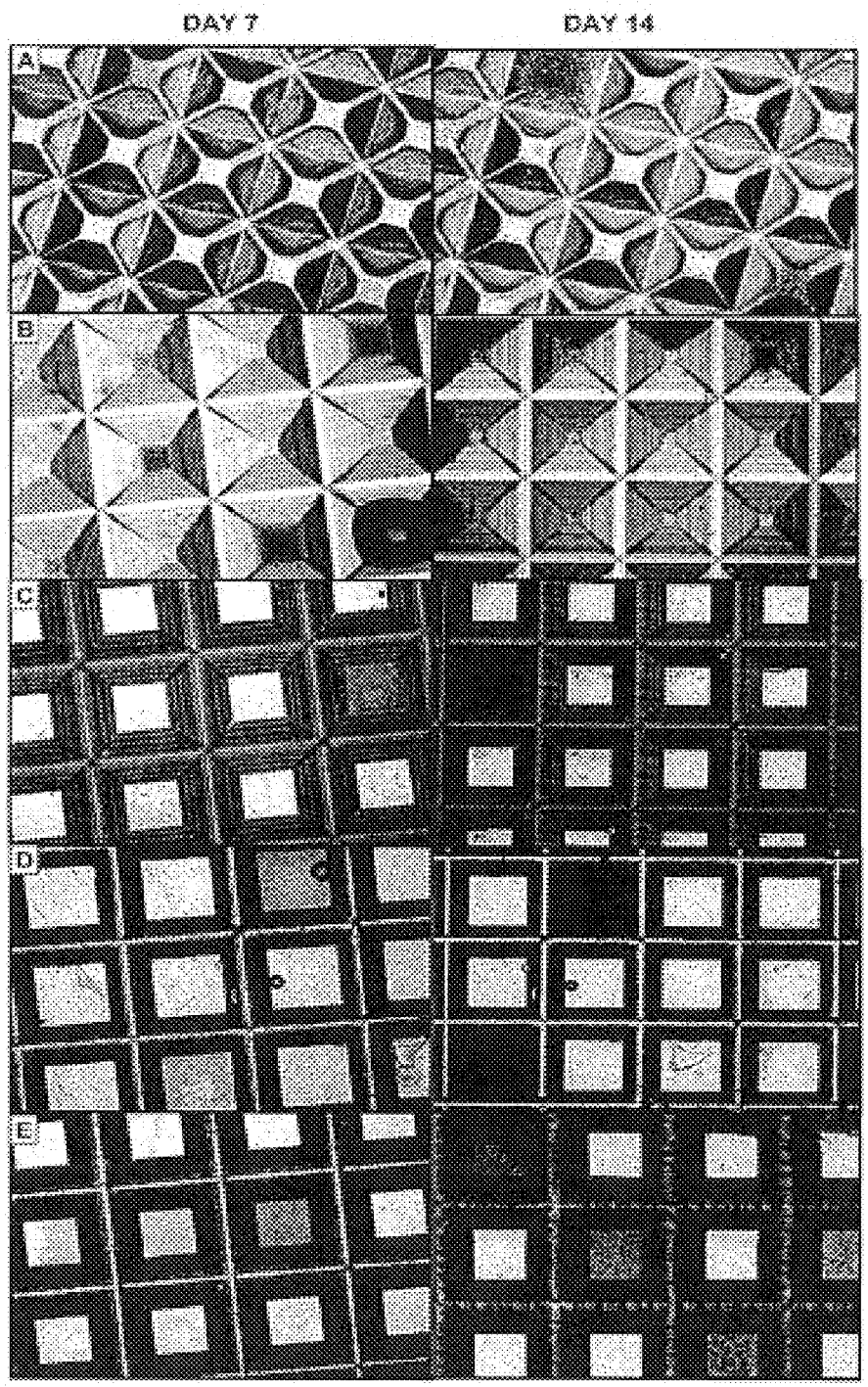
FIGS. 10A to 10E are images showing examples of colony formation in different microwell configurations.

FIG. 10 shows characteristics of colony formation in 5 microwell configurations.

With regards to configuration A, at the earlier time in the culture, the colonies can still be seen confined to the microwell bottom portion. Upon continued growth of the culture for a total of 14 days, colonies have overflowed the microwells and cells appear in the majority of wells surrounding the colony containing wells. It is evident that the microwells of this configuration are insufficient to contain colonies after 14 days of culture. Thus, with this configuration, enumeration of progenitor cell number at time of inoculation is not possible.

Referring still to FIG. 10, with regards to configurations B through E, in all cases, confinement of cells to individual wells is observed at the early timepoint in the culture, when the colonies are still small. At the later timepoint in the culture, microwell to microwell spread of cells is seen to be reduced with either an increase in microwell depth or a decrease in wall angle. The configuration with the largest well volume (configuration E) exhibits complete confinement of colonies to individual wells, with no evidence of microwell to microwell spread after 14 days in culture.

An additional experiment was performed with microwell configurations B through E where hematopoietic progenitor cells from human cord blood in liquid media were inoculated at densities of 21 to 26 colonies/cm$^2$ into pre-wet microwells and allowed to settle into the microwells by gravity. Microwells were evaluated for colony formation numbers and colony containment either 7 or 14 days post-inoculation. For both 7-day and 14-day cultures there was an increase in the observed colony number as the wall angle increased as shown in the table below.

|  | Number of Colonies per Well | |
| --- | --- | --- |
| Conformation | 7-day assay | 14-day assay |
| B | 236 ± 26 | 199 ± 16 |
| C | 292 ± 4 | 199 ± 17 |
| D | 275 ± 12 | 186 ± 5 |
| E | 269 ± 5 | 171 ± 14 |

The exception to this trend is configuration B in the 7-day CFC assay. In this assay there was high cell background in all microwells which made it difficult to count the small colonies accurately. This cell background is most likely due to overflow and spread to adjacent microwells at a high rate because of the shallow wall angle. These data show that for microwells having an aspect ratio in the range of 1.9:1 to 1.1:1, it may also be desirable for the wall angle to be less than 30 degrees, and more specifically, less than 20 degrees.

Example 4

Evaluation of Cell Culture Devices Including Sub-Microwells

Human hematopoietic progenitor cells in liquid medium were inoculated into cell culture dishes containing a set of sub-microwells within each microwell. The microwells within the cell culture device were square at the microwell top portion, and had a microwell width of 1.0 mm, a microwell depth 105 of 1.0 mm, and a wall angle of 15 degrees. The sub-microwells were square at the sub-microwell top portion, had a microwell width of 0.37 mm, a microwell depth of 0.5 mm, and a wall angle of 15 degrees.

Figure 11:
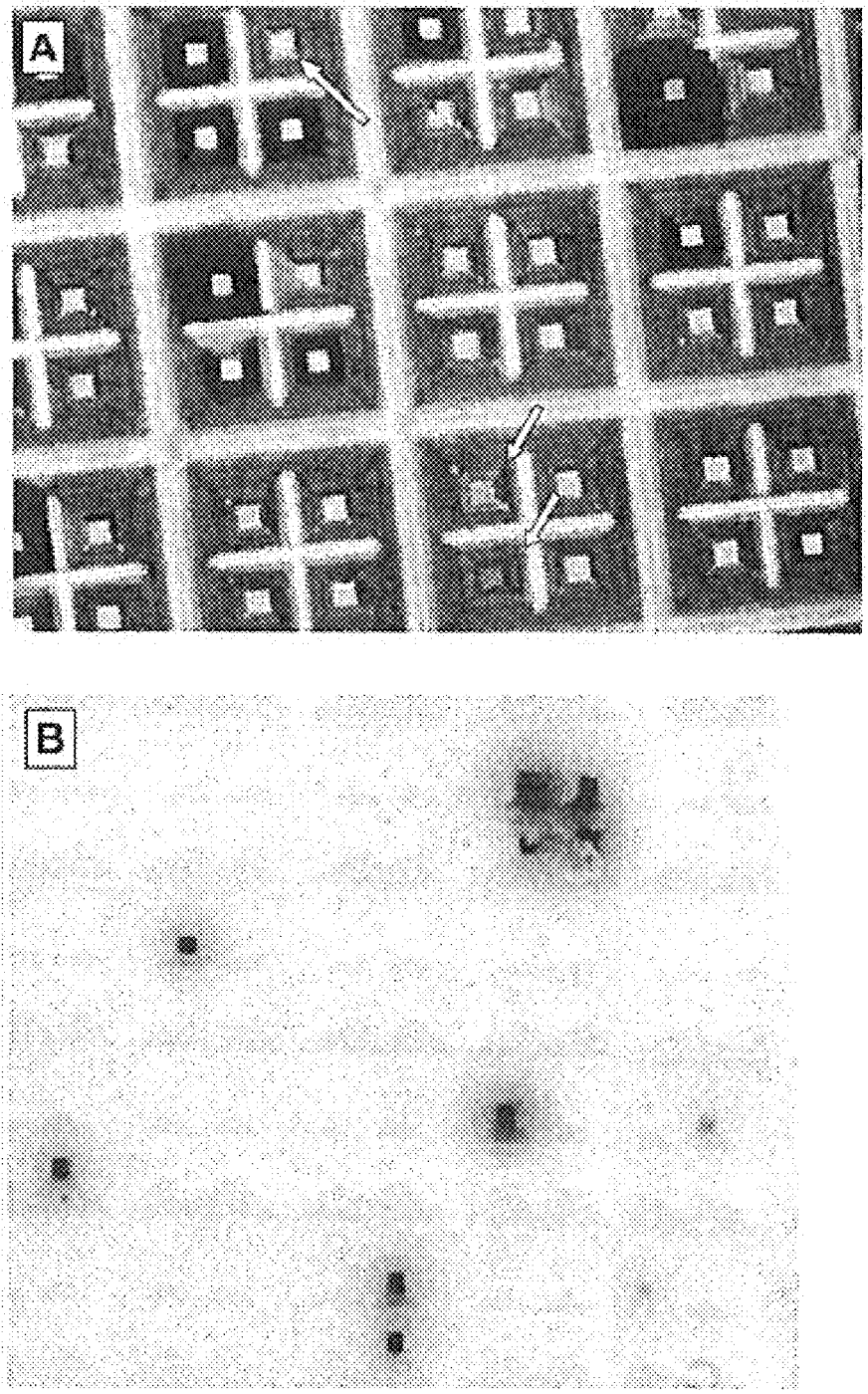
FIG. 11A is an image acquired by brightfield microscopy of a cell culture device including microwells, and sub-microwells within the microwells.
FIG. 11B is an image acquired using a colour CCD scanner of a cell culture device including microwells, and sub-microwells within the microwells.

The cell culture devices were inoculated with a colony density of approximately 7 colonies/cm$^2$ and cells were sedimented into the sub-microwells by slow speed centrifugations. The inoculated cell culture devices were subsequently incubated in a permissive culture environment of 37° C. and a humidified atmosphere containing 5% CO$_2$. Cultures were observed after 7 days of incubation for colony formation by brightfield microscopy and imaged using a CCD digital camera (FIG. 11A). Wells indicated by arrows contain colonies derived from hematopoietic stem cell progenitors after incubation at 37° C. for 7 days. The cells were subsequently stained using the viable cell marker MTT (3-(4,5-dimethylthiazol-2-yl)-2,5-diphenyltetrazolium bromide) in order to visualize the colonies by macroscopic analysis using a CCD colour scanner (FIG. 11B). Briefly, this staining method consisted of incubating the culture in a medium containing MTT until adequate colour formation was observed. The stained cells were then washed by removal of culture medium (by pipeting) and addition and removal of a suitable wash buffer to the sub-microwells. This wash procedure was repeated until no background colouration was apparent.

The colonies were found to be robustly immobilized within the sub-microwells, and no free-floating cells were visible either before or after the staining and wash procedures. Compact and discrete colonies which can be easily counted by microscopy were observed and equivalent colony counts were obtained using the microscopic and macroscopic methods.

FIG. 11A shows colonies grown in the sub-microwells and FIG. 11B shows staining results. At least 6 positive sub-microwells are evident in this image in addition to a cluster of 4 sub-microwells that are nested together in the upper right corner of the image. Based on the overall colony frequency in this image it is most likely that this group of 4 wells has arisen from a single progenitor that had high proliferation potential and overgrew a sub-microwell. This example clearly shows the advantage of using sub-microwells Example 5

Staining of Colonies

Figure 12:
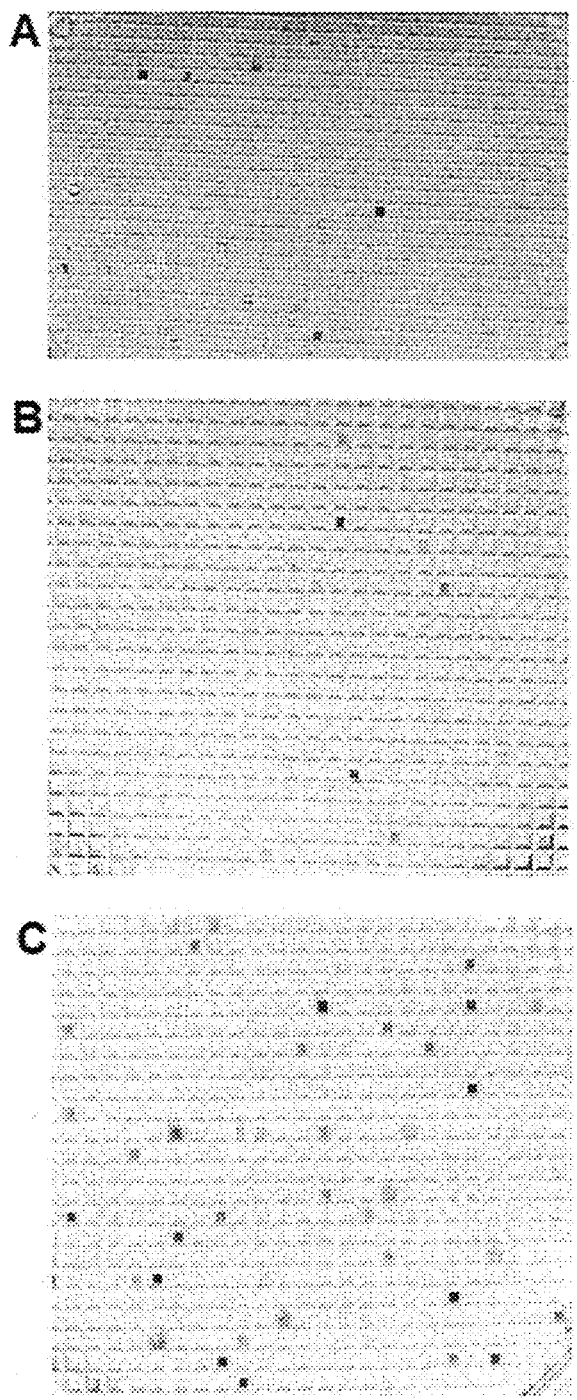
FIGS. 12A to 12C are images of stained colonies in a cell culture device including microwells, obtained using a CCD line sensor (EPSON V500 scanner with MATRIXCCD® 12-line, color sensor)

Three staining methods commonly used for staining of biological and cell culture samples were evaluated in cell culture dishes containing microwells of various configurations. The cell culture devices tested in this example did not contain sub-microwells. The methods included (a) labelling of cells with an antibody to a cell surface marker coupled to the enzyme alkaline phosphatase (AP) followed by addition of the naphtol phosphate substrate and Fast-Red chromogen to result on production of a red precipitate, (b) viable cell staining using MTT (3-(4,5-dimethylthiazol-2-yl)-2,5-diphenyltetrazolium bromide) as a metabolic substrate that is converted to a visible dye by live cells, and (c) non-specific staining using the histological counterstain Evans Blue. For each staining method, the colony containing cell culture devices were first washed by removal of culture medium (by pipeting) and addition of a suitable wash buffer to the microwells, followed by removal of the wash buffer after a short incubation period. This wash procedure was repeated as necessitated by each of the staining protocols. The results of the staining are shown in FIG. 12.

FIG. 12A is an example of colonies stained with an alkaline phosphatase coupled antibody. The colonies are contained within a cell culture device having microwells that are square at the microwell top portion, have a microwell width of 0.8 mm, a wall angle of 15 degrees and a microwell depth of 0.5 mm. Colonies were distinctly stained with a red colour, with minimal background staining. In addition, no evidence of disturbance to the colonies when subjected to the staining procedures was observed. FIGS. 12B and 12C show colonies contained in cell culture device having microwells that are square at the microwell top portion, have a microwell width of 1.0 mm opening, a wall angle of 15 degrees, and a microwell depth of 1.0 mm. The colonies are stained with Evans Blue and MTT respectively. As with the antibody labelling method, no evidence of colony disturbance was observed and colonies were stained with a high level of contrast from the background.

Example 6

Quantification of Colony Forming Progenitor Cells

Colony forming cultures of hematopoietic progenitor cells were conducted in a cell culture device in liquid culture concurrently with standard colony forming cell assay culture of the same cell samples in semisolid medium. The cell culture devices tested in this example did not contain sub-microwells. Cell suspensions in liquid culture medium were inoculated into cell culture devices having microwells that were square at the microwell top portion, have a microwell width of 1.0 mm, a microwell depth of 1.0 mm, and a wall angle of 15 degrees. Cells were sedimented into the microwells by slow speed centrifugation. Suspensions of the same cell samples in semisolid medium (Methocult™, Stemcell Technologies) were inoculated into standard cell culture dishes. In either case, the dishes were inoculated with a colony density of approximately 5 to 15 colonies/cm$^2$ and were subsequently incubated in a permissive culture environment of 37° C. and a humidified atmosphere containing 5% $CO_2$. Colony formation was evaluated after 14 days of culture and total colony number was compared.

Figure 13:
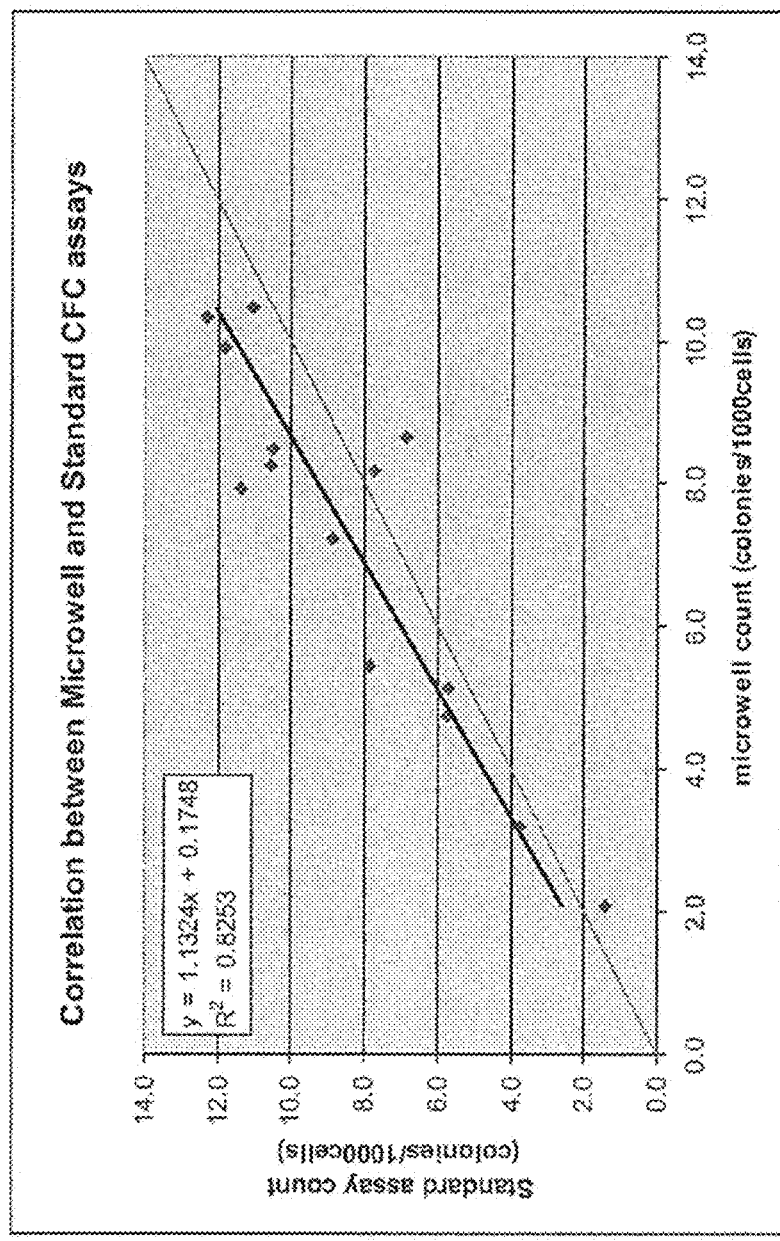
FIG. 13 is a graph showing the correlation between enumeration of stem cell progenitors in cell culture devices including microwells and standard CFC assays.

FIG. 13 illustrates the correlation between colony numbers observed in a cell culture device including microwells and a standard cell culture dish (standardized to number of colonies per 1000 cell inoculated into the dishes). A significant correlation with a slope of approximately 1 demonstrates good agreement of colony assays in cell culture devices including microwells with the current standard CFC assays. The cell culture devices described in this application thereby provide a suitable method of quantification of colony forming progenitor cells.

Example 7

Linear Range of CFC Assays

Cell culture devices including microwells were pre-wet with liquid media by slow speed centrifugation. The cell culture devices tested in this example did not contain sub-microwells. The microwells tested in this example were square at the microwell top portion, had a microwell width of 1 mm, a microwell depth of 1 mm, and a wall angle of 15 degrees. Liquid suspensions of hematopoietic progenitor cells from frozen ficolled human cord blood were inoculated into the cell culture devices and allowed to settle into the microwells by gravity at expected densities of approximately 7 to 57 colonies/cm$^2$ with cell concentration increased step wise from $1\times10^4$ cells/microwell up to $1\times10^5$ cells/microwell. The cell culture devices were incubated in a permissive culture environment of 37° C. and a humidified atmosphere containing 5% $CO_2$. Cell culture devices were evaluated at 7 days post-inoculation for total colony numbers.

Figure 14:
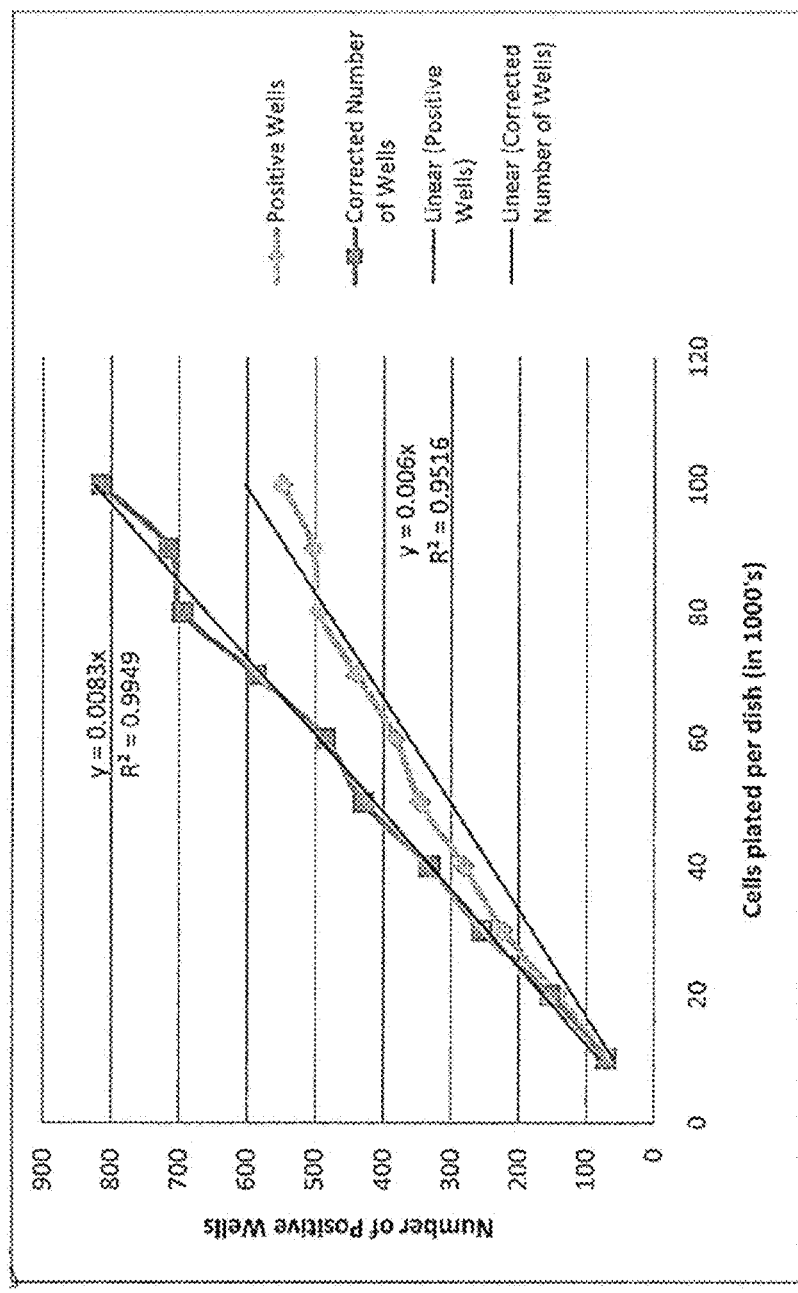
FIG. 14 is a graph showing the increased linear range for the microwell-based CFC assay when using the Poisson distribution to correct for multiple colony forming cells seeded per microwell.

In FIG. 14, the number of positive wells (data points shown as diamonds) does not increase linearly with cell inoculation concentration. Positive wells can originate from a single progenitor, or from more than one progenitor. The more progenitors added to a given microwell culture vessel (a function of progenitor frequency, cell concentration, and volume added), the higher the probability of seeding more than one progenitor per microwell. In this example, the culture vessel has approximately 1000 microwells and thus about 50% are positive at the highest number of cells plated per dish. Based on the observed frequency of positive wells, the Poisson distribution can be used to linearize the output of the assay by determining the expected number of progenitors needed to generate the number of positive well. FIG. 14 shows that once this correction is applied, the relationship between cells plated and number of progenitors is linear (data points shown as squares). The corrected number represents the estimate of the total number of progenitors in the initial sample.

Example 8

Magnetic Separation of Colony Forming Progenitor Cells

Cell culture devices having microwells of the same configuration of Example 7 were wetted with an aqueous buffer (PBS containing 2% FBS) to remove any air trapped in the microwells. A sample of human cord blood was enriched for mononuclear cells by Ficoll (STEMCELL TECHNOLOGIES, 07907) density gradient centrifugation and cells were resuspended in the above buffer. This cell suspension was mixed with dextran coated magnetic microparticles (STEMCELL TECHNOLOGIES, D-microparticles) and an anti-dextran/anti-CD34 antibody cocktail (STEMCELL TECHNOLOGIES, CD34+ selection cocktail). After incubation to allow specific binding of hematopoietic progenitor cells in the suspension to the magnetic microcarriers, the mixture was added to the cell culture devices. The cell culture devices were then placed on a flat magnet (LIFESEP 384F). The microcarriers were seen to migrate downward along the magnetic field gradient to be sedimented into the microwells. The suspension was observed to clear within a period of less than 2 minutes while dark deposits were seen to form on the microwell bottom surfaces. The excess supernatant was removed by pipeting and replaced with liquid culture medium containing cytokines to enable the proliferation of hematopoietic progenitor cells. Additional cultures in cell culture devices of the same configuration and in semisolid medium were inoculated as controls, as described in Example 6 above. The cell culture devices and controls were incubated in a permissive environment (37° C., 5% $CO_2$, humidified incubator) for a period of 7 days and observed for formation of cell colonies within the wells.

Figure 15:
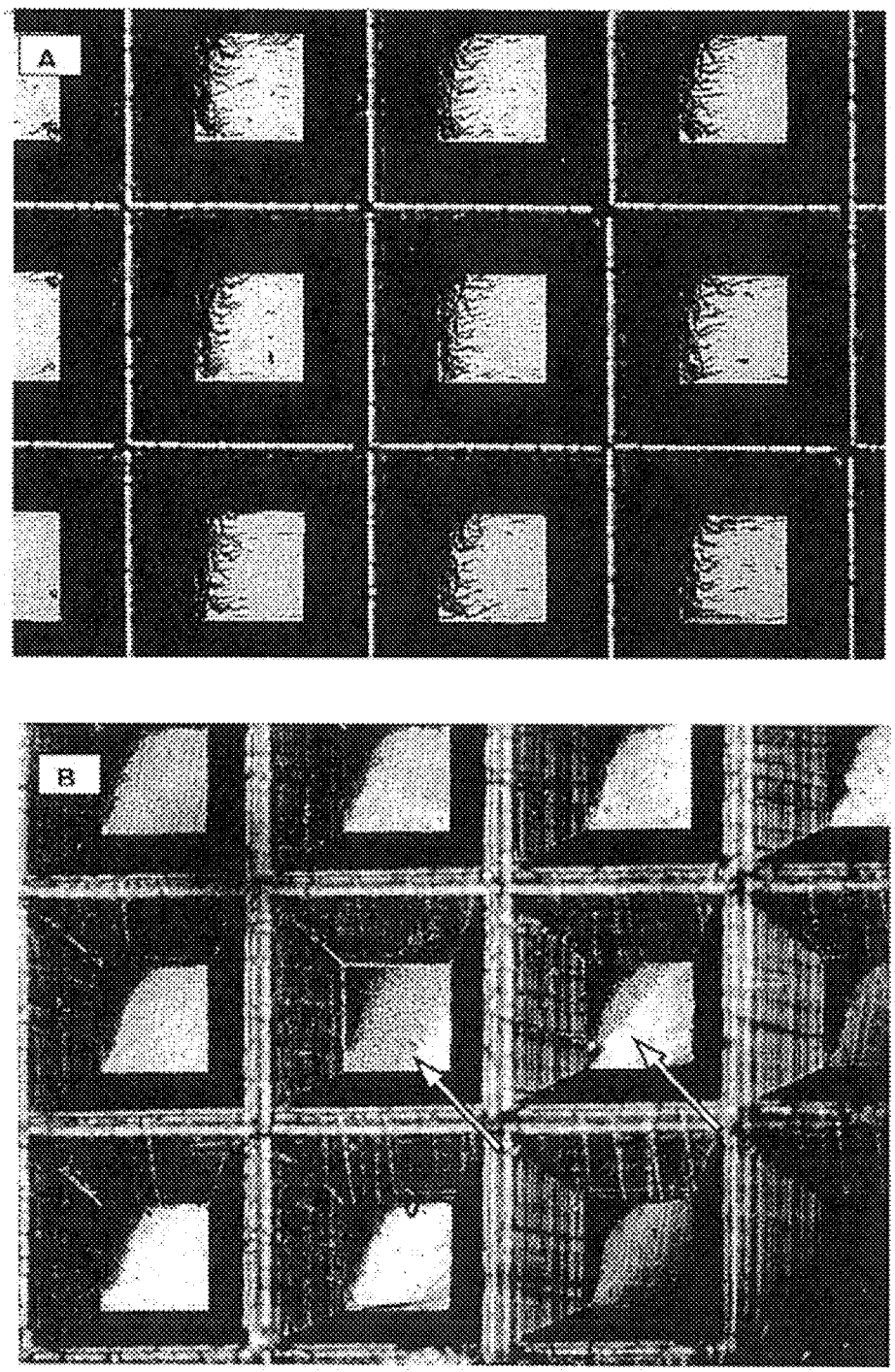
FIG. 15A is an image acquired by brightfield microscopy of microwells containing magnetic microcarrier beads.
FIG. 15B is an image acquired by brightfield microscopy of the microwells of FIG. 14A after incubation for 7 days.
Figure 16:
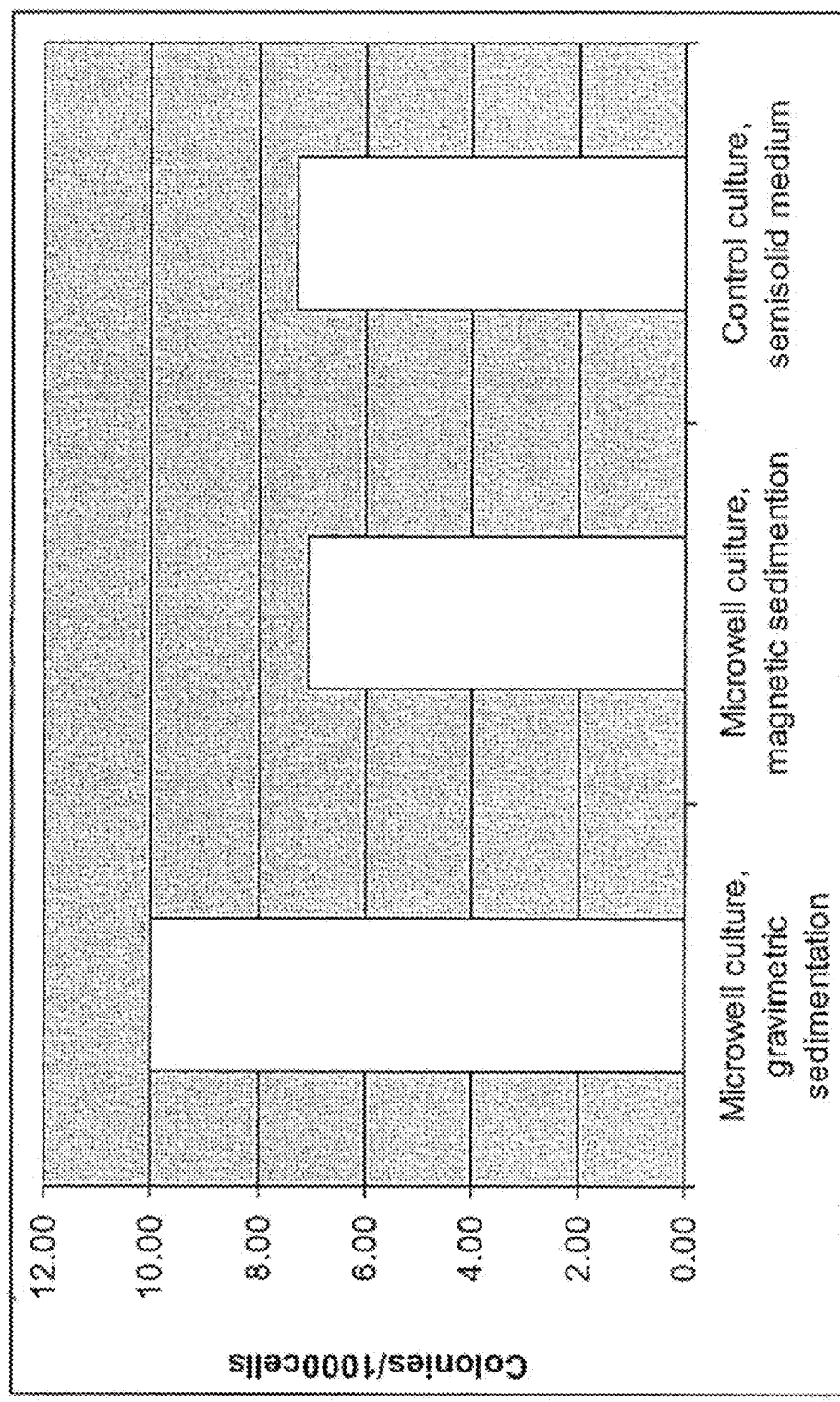
FIG. 16 is a graph showing that magnetic force assisted sedimentation does not affect colony formation in microwell-based CFC assays.

Observation by brightfield microscopy revealed a uniform distribution of the microcarrier beads among the microwells of the cell culture devices. However, within individual microwells, the beads were found to collect towards the edge of the microwell, corresponding to the direction of the magnetic field gradient (FIG. 15A). While individual cells were obscured by the magnetic beads following the inoculation, after 7 days in culture, colonies could be observed to form in individual wells throughout the cell culture device (FIG. 15B). The total colony count in cell culture devices where hematopoietic progenitor cells were selectively sedimented using the magnetic microcarriers was equivalent to colony counts observed in control cell culture devices and cultures conducted in semisolid medium in Petri dishes (FIG. 16). This illustrates that quantitative colony assays for specific cell types can be conducted in cell culture devices including microwells, by selective sedimentation of the desired cells into the microwells with the use of magnetic microcarriers and an antibody cocktail specific to unique markers on the cell surface.

The invention claimed is:
1. A cell culture device comprising:
a well defined by at least one well sidewall and a well bottom wall;
a plurality of microwells within the well, each microwell defined by at least one microwell sidewall extending upwardly from the well bottom wall and separating a microwell fluid volume from a microwell fluid volume of an adjacent microwell and a first common fluid vol- ume within the well above the microwells, wherein microwell sidewalls between adjacent microwells converge to form an apex; and a set of sub-microwells within each microwell for containing one or more cells within each sub-microwell, and a second common fluid volume within each microwell above the set of sub-microwells, each sub-microwell comprising a sub-microwell top portion, a sub-microwell bottom portion and at least one sub-microwell sidewall extending upwardly from the well bottom wall separating a sub-microwell fluid volume from a sub-microwell fluid volume of an adjacent sub-microwell.

2. The cell culture device of claim 1, wherein each sub-microwell is further defined by a portion of one of the microwell sidewalls.

3. The cell culture device of claim 1, wherein the well bottom wall is transparent or translucent.

4. The cell culture device of claim 1, wherein each set of sub-microwells comprises four sub-microwells arranged in a 2×2 array.

5. The cell culture device of claim 1, wherein each set of sub-microwells comprises sub-microwells arranged in a 2×1, 3×1, 3×2, 3×3 or larger array.

6. The cell culture device of claim 1, wherein each sub-microwell tapers in cross-sectional area going from the sub-microwell top portion to the sub-microwell bottom portion.

7. The cell culture device of claim 1, wherein each microwell is frustoconical or frustopyramidal.

8. The cell culture device of claim 1, wherein each sub-microwell is frustoconical or frustopyramidal.

9. The cell culture device of any claim 1, wherein each microwell comprises a microwell top portion and a microwell bottom portion, and each microwell tapers in cross-sectional area going from the microwell top portion to the microwell bottom portion.

10. The cell culture device of claim 1, wherein the sub-microwells, microwells, and well are integrally formed.

11. The cell culture device of claim 1, further comprising a magnetic or magnetizable member positioned below the sub-microwells.

12. The cell culture device of claim 11, wherein the magnetizable member is a wire grid, the well is defined at least in part by a well bottom wall, and the wire grid is embedded within the well bottom wall.

13. The cell culture device of claim 1, wherein each microwell has a microwell top portion and an opposed microwell bottom portion, and the top portion of each microwell has a microwell width of at least 100 microns.

14. The cell culture device of claim 13, wherein each microwell has a microwell depth between the top portion and the bottom portion of at least 75 microns.

15. The cell culture device of claim 1, wherein each microwell has a microwell top portion and a microwell bottom portion, and each microwell comprises a largest dimension at the microwell top portion, and a microwell depth between the microwell top portion and the microwell bottom portion, and the ratio of the largest dimension to the microwell depth is between 1.1:1 and 1.9:1.

16. The cell culture device of claim 1, each microwell comprising a microwell top portion and a microwell bottom portion, each microwell comprising a largest dimension at the microwell top portion, and a microwell depth between the microwell top portion and the microwell bottom portion, wherein each microwell tapers in cross-sectional area going from the microwell top portion to the microwell bottom portion and the ratio of the largest dimension to the microwell depth is between 1.1:1 and 1.9:1.

17. The cell culture device of claim 16, wherein the largest dimension is at least 140 microns.

18. The cell culture device claim 16, wherein the microwell depth is at least 75 microns.

19. The cell culture device of claim 16, wherein each microwell is frustoconical or frustopyramidal.

20. The cell culture device of claim 16, wherein each sub-microwell is frustoconical or frustopyramidal.

21. The cell culture device of claim 16, wherein the well is defined at least in part by at least one well sidewall, and a well bottom wall.

22. The cell culture device of claim 21, wherein the well bottom wall is transparent or translucent.

23. The cell culture device of claim 16, further comprising a magnetic or magnetizable grid positioned below the microwells.

24. The cell culture device of claim 23, wherein the well is defined at least in part by a well bottom wall, and the grid is embedded within the well bottom wall.

25. The cell culture device of claim 16, wherein the microwells and well are integrally formed.

26. The cell culture device of claim 16, wherein the sub-microwells are integrally formed with the microwells and well.

27. The cell culture device of claim 16 wherein each set of sub-microwells comprises four sub-microwells arranged in a 2×2 array.

28. The cell culture device of claim 16, wherein each sub-microwell tapers in cross-sectional area going from the sub-microwell top portion to the sub-microwell bottom portion.

29. The cell culture device of claim 16, further comprising a second common fluid volume within each microwell above the set of sub-microwells.

30. The cell culture device of claim 16, wherein the angle of the microwell sidewall with respect to the vertical is less than 30 degrees.

* * * * *